(12) United States Patent
Sun et al.

(10) Patent No.: US 9,934,566 B2
(45) Date of Patent: *Apr. 3, 2018

(54) 3-D VESSEL TREE SURFACE RECONSTRUCTION METHOD

(71) Applicant: Siemens Healthcare GmbH, Erlangen (DE)

(72) Inventors: Shanhui Sun, Plainsboro, NJ (US); Stefan Kluckner, Lawrenceville, NJ (US); Ahmet Tuysuzoglu, Plainsboro, NJ (US); Ankur Kapoor, Plainsboro, NJ (US); Günter Lauritsch, Nuremberg (DE); Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 20 days.

This patent is subject to a terminal disclaimer.

(21) Appl. No.: 15/207,540

(22) Filed: Jul. 12, 2016

(65) Prior Publication Data

US 2017/0018116 A1 Jan. 19, 2017

Related U.S. Application Data

(60) Provisional application No. 62/192,194, filed on Jul. 14, 2015.

(51) Int. Cl.
| | |
|---|---|
| *G06T 15/00* | (2011.01) |
| *G06T 7/00* | (2017.01) |
| *A61B 6/00* | (2006.01) |
| *G06T 11/00* | (2006.01) |
| *A61B 6/03* | (2006.01) |

(52) U.S. Cl.
CPC ............ *G06T 7/0012* (2013.01); *A61B 6/032* (2013.01); *A61B 6/504* (2013.01); *A61B 6/5211* (2013.01); *A61B 6/541* (2013.01); *G06T 11/003* (2013.01)

(58) Field of Classification Search
None
See application file for complete search history.

(56) References Cited

U.S. PATENT DOCUMENTS

| | | | |
|---|---|---|---|
| 2002/0136440 A1 | 9/2002 | Yim | |
| 2006/0140473 A1* | 6/2006 | Brooksby | G01N 21/9515 382/154 |

(Continued)

OTHER PUBLICATIONS

Blondel, Christophe, et al. "Reconstruction of coronary arteries from a single rotational X-ray projection sequence." IEEE Transactions on Medical Imaging 25.5 (2006): 653-663.

(Continued)

*Primary Examiner* — Weiming He (57) ABSTRACT

A method for reconstructing 3-D vessel geometry of a vessel includes: receiving a plurality of 2-D rotational X-ray images of the vessel; extracting vessel centerline points for normal cross sections of each of the plurality of 2-D images; establishing a correspondence of the centerline points; constructing a 3-D centerline vessel tree skeleton of the vessel; constructing an initial 3-D vessel surface having a uniform radius normal to the 3-D centerline vessel tree skeleton; and constructing a target 3-D vessel surface by deforming the initial vessel surface to provide a reconstructed 3-D vessel geometry of the vessel.

18 Claims, 7 Drawing Sheets

(56) References Cited

U.S. PATENT DOCUMENTS

| | | | | |
|---|---|---|---|---|
| 2009/0141968 | A1* | 6/2009 | Sun | G06T 7/55 |
| | | | | 382/154 |
| 2013/0216110 | A1* | 8/2013 | Zheng | G06K 9/34 |
| | | | | 382/128 |
| 2015/0310607 | A1* | 10/2015 | Grady | G06F 19/3437 |
| | | | | 382/131 |
| 2017/0098311 | A1* | 4/2017 | Abramoff | G06T 7/162 |

OTHER PUBLICATIONS

Blondel, Christophe, et al. "3D tomographic reconstruction of coronary arteries using a precomputed 4D motion field." Physics in medicine and biology 49.11 (2004): 2197-2208.

Boykov, Yuri, and Vladimir Kolmogorov. "An experimental comparison of min-cut/max-flow algorithms for energy minimization in vision." IEEE transactions on pattern analysis and machine intelligence 26.9 (2004): 1124-1137.

Wu, Xiaodong, and Danny Z. Chen. "Optimal net surface problems with applications." International Colloquium on Automata, Languages, and Programming. Springer Berlin Heidelberg, (2002): 1029-1042.

Frangi, Alejandro F., et al. "Multiscale vessel enhancement filtering." International Conference on Medical Image Computing and Computer-Assisted Intervention. Springer Berlin Heidelberg, (1998): 130-137.

\* cited by examiner

3-D VESSEL TREE SURFACE RECONSTRUCTION METHOD

CROSS REFERENCE TO RELATED APPLICATION

This application claims the benefit of U.S. Provisional Application Ser. No. 62/192,194, filed Jul. 14, 2015, which is incorporated herein by reference in its entirety.

BACKGROUND

The present disclosure relates generally to a three-dimensional (3-D) vessel tree surface reconstruction method, particularly to a 3-D coronary artery tree surface reconstruction method, and more particularly to a 3-D coronary artery tree surface reconstruction method from a limited number of two-dimensional (2-D) rotational X-ray angiography images.

In percutaneous coronary intervention (PCI) procedures, physicians evaluate and identify coronary artery lesion (stenosis), and prepare catheterization utilizing X-Ray coronary angiographic images. These images are 2-D projection images of a complex coronary artery tree acquired by X-Ray machines called C-Arms either from bi-plane or from mono-plane. 2-D projections cause vessel occlusion, crossing, and foreshortening. To better understand vessel geometry, usually multiple views with different angles are acquired. In addition, 2-D projection image based quantitative coronary analysis (QCA) is usually chosen to determine lesion length and stent size during PCI. However, there are two major limitations of 2-D QCA: foreshortening and out-of-plane magnification errors.

Known in the art there are two major categories of 3-D reconstruction of coronary arteries from angiographic images: tomographic reconstruction, and symbolic surface reconstruction. In some approaches of performing 3-D tomographic reconstruction of coronary arteries, motion artifact was minimized through a pre-computed 4-D motion field. The 4-D motion field is computed from 3-D coronary artery centerline reconstruction and a 4-D parametric motion model fitting. However, tomographic based approach is computation expensive. In addition, it needs sufficient view angles and a limited number of images can cause a blur and low resolution reconstruction. 3-D symbolic reconstruction has been investigated using two projections and multiple projections. The mainstream idea among existing approaches is to reconstruct a 3-D vessel skeleton and then either fit an elliptical model representing a vessel cross-section using 2-D measurement (e.g. segmentation), or estimating vessel radii from 2-D measurement. The focus here is on developing different centerline reconstruction approaches but not surface reconstruction. Elliptical or circular models are symbolic and are not accurate due to lumen deformation and lesion. Siemens Healthcare has developed software offering 3-D symbolic vessel surface visualization and 3-D QCA of lesions and segment anatomy. However, this software is limited by 2 views, and semi-automated 2-D lumen segmentation has to be performed. 2-D vessel lumen segmentation on the projection image is a challenging task due to vessel occlusion and crossing. Therefore, many iterations of user intervention are needed to get a good segmentation for further symbolic surface reconstruction.

While existing vessel reconstruction methods usable in PCI procedures may be suitable for their intended purpose, the art of PCI procedures would be advanced with a method to automatically generate 3-D vessel geometry and perform 3-D QCA in PCI procedures. 3-D vessel geometry including lumen could avoid the limitations from 2-D projection images. 3-D QCA would therefore allow quantitative determination of vessel lumen, grade of stenosis, and virtual fractional flow reserve (FFR).

This background information is provided to reveal information believed by the applicant to be of possible relevance to the present invention. No admission is necessarily intended, nor should be construed, that any of the preceding information constitutes prior art against the present invention.

SUMMARY

An embodiment includes a method for reconstructing 3-D vessel geometry of a vessel, comprising: receiving a plurality of 2-D rotational X-ray images of the vessel; extracting vessel centerline points for normal cross sections of each of the plurality of 2-D images; establishing a correspondence of the centerline points; constructing a 3-D centerline vessel tree skeleton of the vessel; constructing an initial 3-D vessel surface having a uniform radius normal to the 3-D centerline vessel tree skeleton; and constructing a target 3-D vessel surface by deforming the initial vessel surface to provide a reconstructed 3-D vessel geometry of the vessel.

An embodiment includes a computer program storage medium comprising a non-transitory computer readable medium having program code executable by a processing circuit for implementing the above noted method.

An embodiment includes an apparatus for reconstructing 3-D vessel geometry of a vessel, comprising: a computer controlled machine comprising a processing circuit; and computer readable executable instructions, which upon loading into the processing circuit causes the machine to be responsive to the executable instructions to facilitate implementation of the above noted method.

The above features and advantages and other features and advantages of the invention are readily apparent from the following detailed description of the invention when taken in connection with the accompanying drawings.

BRIEF DESCRIPTION OF THE SEVERAL VIEWS OF THE DRAWINGS

Referring to the exemplary non-limiting drawings wherein like elements are numbered alike in the accompanying Figures:

FIG. 2 (b) depicts the normal directions for two overlapping (very close) points that belong to different vessel branches for use in accordance with an embodiment;

DETAILED DESCRIPTION

Although the following detailed description contains many specifics for the purposes of illustration, anyone of ordinary skill in the art will appreciate that many variations and alterations to the following details are within the scope of the claims. Accordingly, the following example embodiments are set forth without any loss of generality to, and without imposing limitations upon, the claimed invention.

An embodiment includes a method to reconstruct a 3-D vessel tree surface, coronary artery for example, from a limited number of 2-D rotational X-ray angiography images. First, a limited number of views with a same cardiac phase are identified from the X-ray angiography images using Electrocardiography (ECG) signals (or ECG gated acquisition signals). Second, vessel centerlines of those 2-D images are extracted utilizing a known technique of model-guided extraction of coronary vessel structures in 2-D X-ray angiograms. The correspondence of centerline points are identified using a prior 3-D vessel shape segmented from DynaCT reconstruction, using shape properties such as vessel tangents and normals, and solving an assignment problem. The best match between a prior 3-D model constrains the assignment problem. In one embodiment, the prior segmented shape can be obtained from a DynaCT volume. For the generation of a DynaCT volume, we utilize known approaches such as interventional 4D motion estimation and reconstruction of cardiac vasculature without motion periodicity assumption, or ECG-gated interventional cardiac reconstruction for non-periodic motion, and considering tomographic 3-D/4-D reconstruction. In an embodiment, only one data set is needed for point correspondence and 3-D coronary tree surface reconstruction. Third, a 3-D centerline (vessel tree skeleton) is reconstructed from 2-D points using a bundle adjustment based approach. Fourth, we create the vessel surface reconstruction by finding an optimal surface for the vessel tree skeleton. The sought surface is optimized based on cost functions derived from 2-D images and constrained by the vessel skeleton.

Features of an embodiment of the method disclosed herein include: (1) a fully automated vessel surface reconstruction method (overall pipeline); (2) an alignment estimation between prior models and multiple segmented 2-D structures (a benefit of an embodiment disclosed herein is that multiple landmarks are identified and detected in many views, compared to other techniques that consider only one landmark, which contemplates a significant improvement in accuracy); (3) a centerline reconstruction algorithm is proposed (a reconstructed 3-D centerline is expected to have higher precision and accuracy for lumen surface reconstruction than a centerline previously derived from DynaCT even ECG-gating from the same cardiac phase being utilized, which contemplates more accurate projections resulting from a centerline reconstruction process); (4) an assignment problem constrained by using model alignment that considers vessel tangents and normals during the alignment phase; (5) an embodiment includes a best alignment based between multiple 2-D projections and a 3-D model based on costs derived from vessel tangents and normals; (6) an embodiment includes a best assignment by utilizing a prior 3-D model as a constraint; (7) while the existing mainstream of vessel surface reconstruction methods are from 2-D to 3-D, an embodiment includes a reconstructed vessel surface in 3-D space driven by a data term that is derived from 2-D information via back-projection (existing methods rely on 2-D vessel segmentation based on which symbolic surface is constructed, which require performing 2-D vessel lumen segmentation or finding 2-D vessel boundary correspondence, where both problems are non-trivial due to projection limitations such as vessel occlusion and branch crossing); (8) an embodiment includes 3-D vessel surface reconstruction through solving an optimal graph search problem (the missed data term (cost function) due to a lack of camera views is regularized by a surface smoothness, which contemplates achieving a global optimal solution under a certain graph construction); (9) methods to find a cost function are presented; and, (10) with utilization of an embodiment of 3-D surface reconstruction as disclosed herein, 2-D vessel segmentation can be generated using back-projection.

Figure 1:
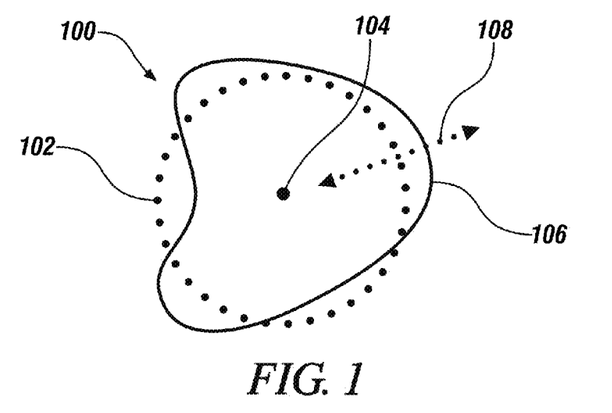
FIG. 1 depicts a model using a 2-D vessel cross section to illustrate vessel surface deformation in accordance with an embodiment.

Reference is now made to FIG. 1, which illustrates a model 100 in accordance with an embodiment using a 2-D vessel cross section (normal to a centerline of the vessel) to illustrate vessel surface deformation. The solid-line curve depicts a target vessel surface. The dotted-line curve 102 depicts an initial vessel boarder having a centerline point 104. An initial vessel surface (synthetic vessel surface, e.g. a tubular structure with uniform radius), also referred to by reference numeral 102, is constructed around the centerline 104 and evolves towards a true (target) vessel surface 106. In this way, the surface reconstruction problem (finding the true vessel surface 106) is transformed into finding an optimal vessel surface problem (establishing the synthetic initial vessel surface 102). The arrow 108 depicts a deformation direction of the initial vessel surface point of 102 that is driven by image information collected from all corresponding 2-D projection views. At the same time, surface smoothness is enforced to make sure a feasible surface results. As such, an embodiment of the method does not need to compute 2-D vessel segmentation or find sufficient corresponding 2-D vessel boundary points.

To be able to construct the 3-D vessel centerline 104, point correspondences need to be established between the segmented vessel points across the 2-D images. In an embodiment of the method, the vessel topology is extracted in the form of ordered point sets, Si, from each angiographic image, where i is $i^{th}$ image. The method assumes that each point set Si is the projection of a transformed 3-D centerline model M according to the following:

$$S_i = P_i T(M, \theta_i), \quad \text{Equa. 1}$$

where $P_i$ is the camera projection operator corresponding to image i, and $T(M, \theta_i)$ is a defined transformation model. Given M and $S_i$, the method employs Gaussian mixture models (GMM) to find transformations $T(M, \theta_i)$ that minimize the following cost function:

$$J(S_i, M, \theta_i) = \int (GMM(S_i) - GMM(P_i T(M, \theta_i)))^p dx, \quad \text{Equa. 2}$$

where the energy function $J(Si, M, \theta_i)$ measures the distance of two Gaussian mixture models (GMM) where $p \in [0, 2]$. In some embodiments, when $p=2$, this cost function corresponds to the $l_2$-norm. In such embodiments, a closed-form solution can be utilized. In some embodiments, when $p=1$, the cost function corresponds to $l_1$-norm, corresponding with KL(KullbackLeibler)-divergence of the two GMMs. Such embodiments can be more forgiving to outliers existing in either sets. The GMMs are obtained by treating each point as a separate Gaussian component with its mean being the spatial location of the point along with a user defined spherical covariance matrix. The above framework estimates separate transformations for each of the angiographic images. However, when the 3-D model is not accurate, it introduces errors that propagate to point correspondences. In such cases, a more robust way would be to estimate a single transformation that aligns all of the angiographic images to an averaged motion model and hence, we utilize the minimization of the following energy function:

$$\sum_i^N w_i J(S_i, M, \theta), \quad \text{Equa. 3}$$

where $w_i \in [0, 1]$, $\Sigma w_i = 1$, is the weight associated with image i. Images are analyzed to extract these weights.

Figure 2A:
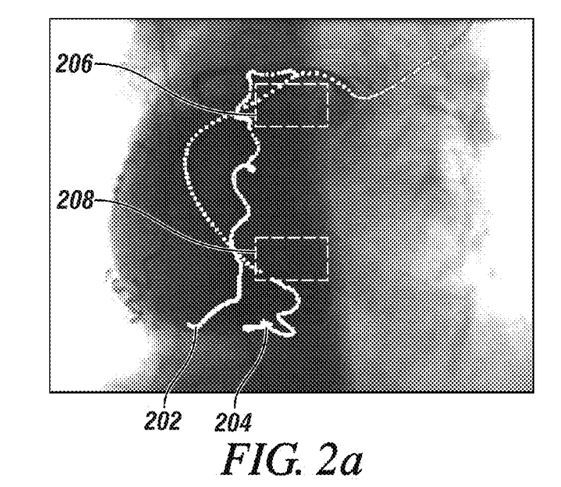
FIG. 2(a) depicts two distinct vessels crossing each other due to camera projection for use in accordance with an embodiment.
Figure 2B:
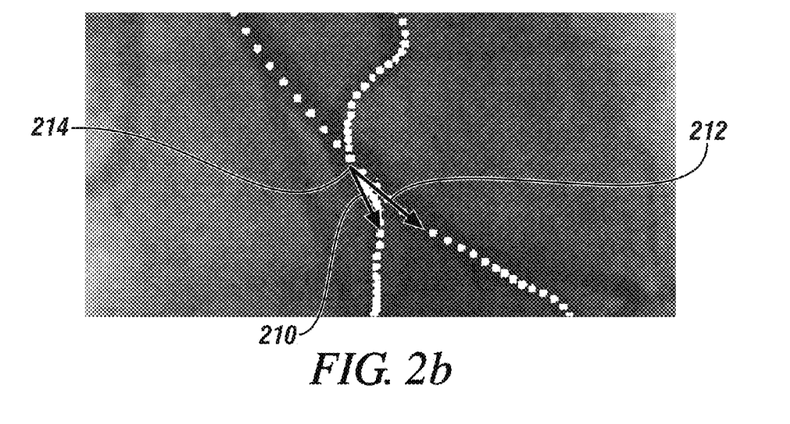

Loss of depth due to camera projection can cause distinct vessels to fall on top of each other. One such example is depicted in FIG. 2(a), which depicts two distinct vessels 202, 204 crossing each other due to camera projection as shown in the two dashed boxes 206, 208. This phenomenon can cause the registration algorithm to get stuck in a poor local minima. Since the segmented point sets have structure, topological information can be used to discriminate between overlapping vessel structures. FIG. 2(b) depicts the normal directions 210, 212 for the two overlapping (very close) vessels 202, 204 associated with box 208 in FIG. 2(a), represented by projected intersection point 214 in FIG. 2(b). Although these overlapping vessels share a similar projected location (projected intersection point 214), their normal directions 210, 212 are very different. This information is utilized in the registration framework by modifying each GMM component to include its normal vector in its mean. Note that this does not change the distance formulation given in Equa. 2. In this embodiment, the overlapping point location $x_{i,j}$ (projected intersection point 214 for example) is augmented to include the unit normal, $x_{i',j}$ at the point. In some other embodiments, the point location can be augmented image derived features such as SURF (Speeded Up Robust Features), SIFT (Scale-Invariant Feature Transform) and FFT (Fast Fourier Transform), for example, at the respective local neighborhood.

Figure 3:
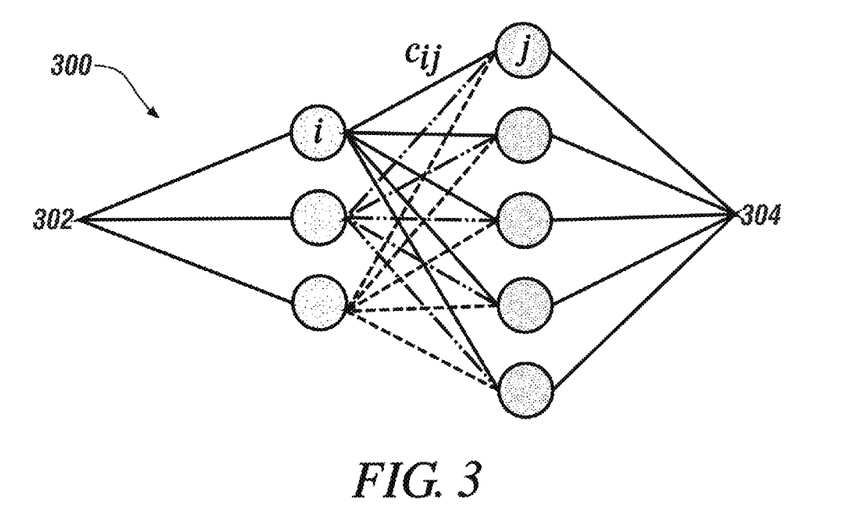
FIG. 3 depicts a bipartite graph corresponding to a linear assignment process in accordance with an embodiment.

Once the registration step is completed, point correspondences are established between the vessel points across the images. These correspondences are solved by finding the matching vessel point for every projected model point in each image. For each image and the model set, this matching is solved via a linear assignment process. As shown in FIG. 3, a first set of vertices 302 represents transformed, projected model points of the vessel centerline points (see 104 in FIG. 1 for example), and a second set of vertices 304 represents the associated segmentation points of a prior 3-D vessel shape of the vessel segmented from a DynaCT volume and DynaCT reconstruction. The vertices 302, 304 are represented as a bipartite graph 300 that corresponds to the linear assignment process. The weights of these edges, $c_{ij}$, can be computed using the distance of spatial locations of the vertices. Furthermore, it can be assumed that if the two vertices are very far apart, they should not be matching. To incorporate this assumption, a distance threshold, $d_{th}$, is used as follows:

$$c_{i,j} = \{d_{i,j} \text{ if } d_{i,j} < dth; \infty \text{ if } d_{i,j\_}d_{th}\}. \quad \text{Equa. 4}$$

Such a thresholding operation makes certain matchings infeasible, and therefore provides robustness in the case of missing vessel segmentations.

Regarding centerline reconstruction, ECG gating helps to compensate cardiac motion, however, it should be noted that the respiratory (breathing) motion also needs to be compensated for to make sure that projection views are coherent with the 3-D reconstruction. The breathing motion can be approximated as a 3-D translation in accordance with known methods. An embodiment of the method compensates this motion by adapting camera projection parameters employing a known bundle adjustment based method. It should also be noted that the remaining rigid transformation due to non-perfect ECG gating can also be compensated in this process. An embodiment of the method iteratively reconstructs the 3-D vessel center-line from corresponding 2-D centerline points and performs bundle adjustment. 3-D centerline and refined camera parameters (3-D to 2-D projection matrix) are computed based on the following equation:

$$\min_{a_j, b_i} \sum_{i=1}^n \sum_{j=1}^m k^{i,j} d(Q(a_j, b_i), x^{i,j}), \quad \text{Equa. 5}$$

where: n is the number of 3-D points that are seen in m views; camera j is parameterized by a vector $a_j$; $b_i$ is the $i^{th}$ centerline point; $Q(a_j, b_i)$ is the projection of 3-D point $b_i$ on image j; $x^{i,j}$ is the $i^{th}$ 2-D centerline point measurement on image j; d( , ) is a Euclidean distance between the associated points defined within the parentheses; and, $k^{i,j} \in [0, 1]$ is a confidence measurement of $x^{i,j}$.

Figure 4:
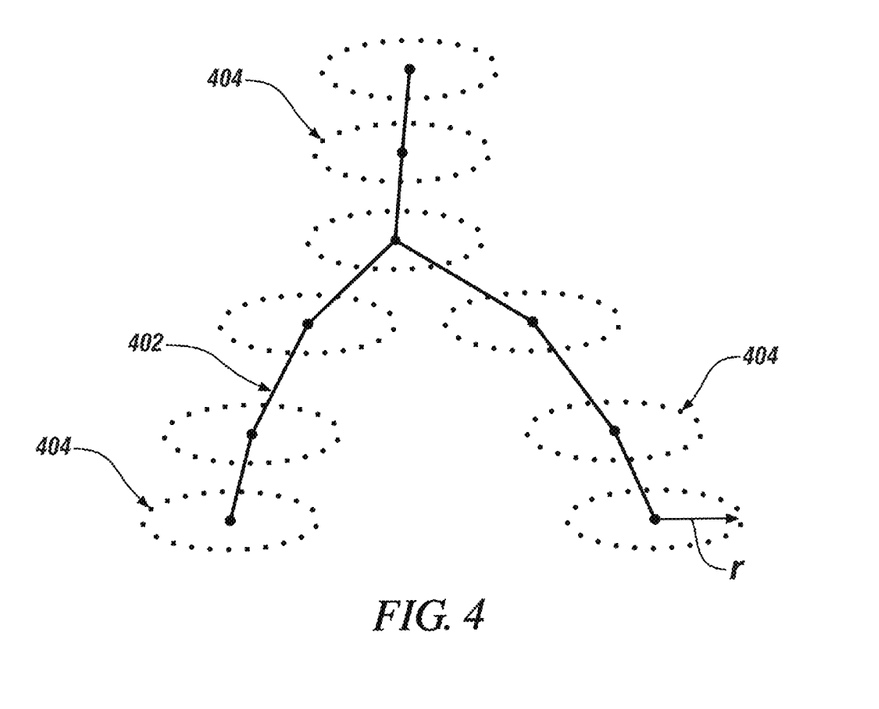
FIG. 4 depicts a point cloud construction around the centerline of a vessel tree skeleton in accordance with an embodiment.
Figure 5A:
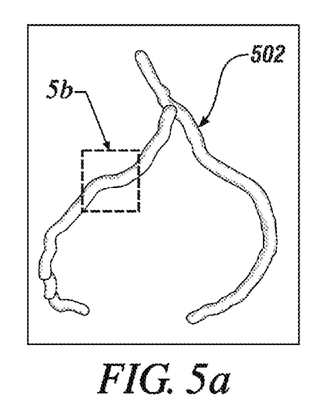
FIG. 5(a) depicts an initial vessel surface (synthetic vessel mesh surface, e.g. a tubular structure with uniform radius) in accordance with an embodiment.
Figure 5B:
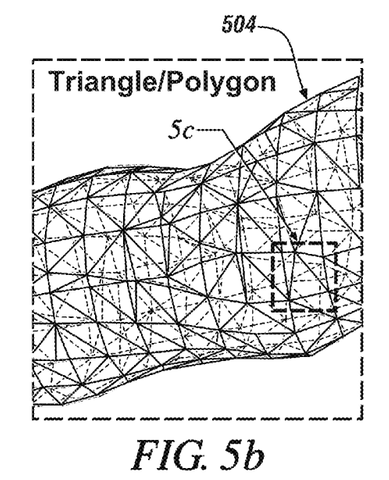
FIG. 5(b) depicts a mesh zoom-in of the mesh of FIG. 5(a) in accordance with an embodiment.

Reference is now made to FIGS. 4, 5(a) and 5(b) regarding surface reconstruction. Around the resulting 3-D centerline 402 (see also centerline point 104 in FIG. 1), an initial mesh surface is computed (best seen with reference to FIGS. 5(a) and 5(b) discussed further below). A point cloud construction 404 is generated around the centerline 402 as depicted in FIG. 4. The dotted-line circles (also referred to by reference numeral 404) depict sampling points around an associated centerline point 104 (see FIG. 1 for example) of centerline 402. It should be noted that these circles 404 are perpendicular to an associated centerline tangential direction 210, 212 (see FIG. 2(b) for example). Sampling points are normally distributed along a normal direction of the corresponding centerline point with radius r. In one embodiment, a Poisson surface reconstruction method is utilized to compute the mesh from the point cloud. An example of an initial mesh surface 502, 504 is depicted in FIGS. 5(a) and 5(b).

Figure 5C:
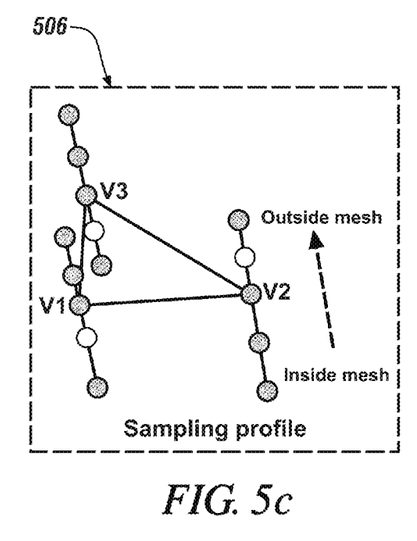
FIG. 5(c) depicts vessel point sampling in 3-D space as performed along a searching profile (e.g. vertex normal direction) for a vertex $V_i$ in accordance with an embodiment.

For each vertex on the initial mesh surface 504, a vector of points is created and contains the final sought surface vertex V. The sampling 506 is performed in the 3-D space along a searching profile for each initial vertex. Note that the searching profile intersects the initial surface covering both inside and outside initial surface. In an embodiment, the searching profile is along the vertex normal direction. The sampling method is illustrated in FIG. 5(c). In an embodiment, sampling distance can be uniform. In an embodiment, the sample distance linearly decreases with the radius. In the 3-D segmentation domain, a deformable shape model is often utilized to segment an object with the known shape. One example can be found in a U.S. patent publication no. 2002/0136440 (hereinafter referred to as the '440 publication), where a 3-D vessel shape is segmented using a deformable shape model in 3-D angiography image data. An embodiment of the method disclosed herein can also utilize a deformable shape model. However, a fundamental difference between an embodiment disclosed herein and the '440 publication is that the 3-D segmentation solution provided herein produces a surface reconstruction from a limited number of 2-D projection images, but not in a volumetric image. In an embodiment, the surface deformation is driven by 2-D information through 3-D to 2-D projection. Due to the lack of views, not all projected surface points are aligned with a 2-D vessel boarder, but instead are inside the vessel. In contrast to 3-D segmentation, an embodiment also addresses additional challenges like vessel occlusion and crossing problem.

Assume that each sampling point has a cost function $w(v_i, S(v_i))$ indicating that the sampling point is unlikely on the sought surface, where $v_i$ is the surface vertex and $S(v_i)$ is any sampling point along a searching profile for $v_i$. We denote $\tau = \{S(v_i) | i=1 \ldots L\}$ as an arbitrary (initial) vessel surface, where L is the number of vertices. The method solves the surface reconstruction by finding a minimum-surface cost subject to smoothness constraints $|S(v_i) - S(v_j)| \leq \Delta$ via the following formula:

$$\tau^* = \operatorname{argmin} \Sigma w(v_i, S(v_i)) \quad \text{Equa. 6}$$
$$\tau \, i = 1 \ldots L$$
$$\text{subject to } |S(v_i) - S(v_j)| \leq \Delta,$$

where $\Delta$ is a smoothness constraint that requires that the surface's position between neighboring vertices $v_i$ and $v_j$ does not change more than a constant distance $\Delta$.

Figure 5D:
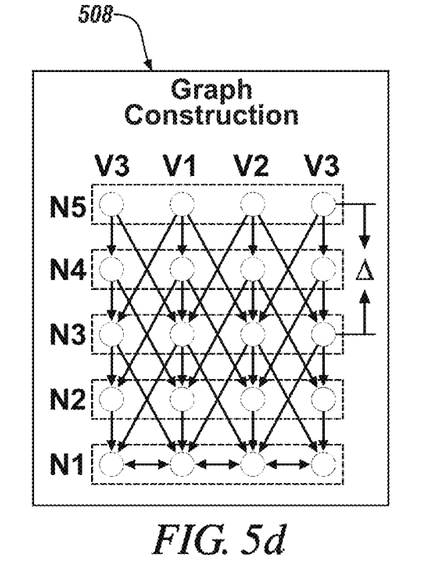
FIG. 5(d) depicts a graph structure that is constructed based on sampling nodes in accordance with an embodiment.
Figure 6A:
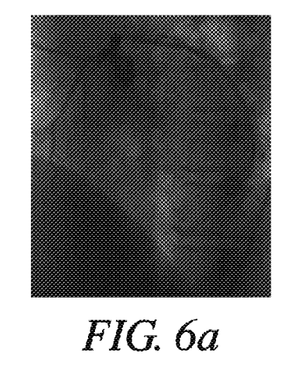
FIGS. 6(a), 6(d), 6(g) and 6(j), the first column, depicts original 2-D rotational X-ray angiography images from four different patients for use in accordance with and embodiment.
Figure 6B:
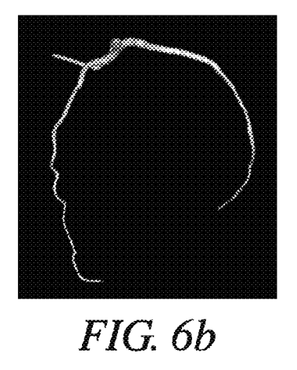
FIGS. 6(b), 6(e), 6(h) and 6(k), the second column, depicts reconstructed vessel surfaces from the same view as the acquired original images in accordance with an embodiment.
Figure 6C:
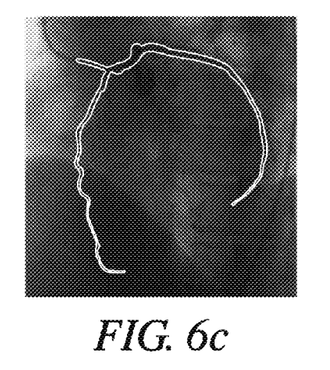
FIGS. 6(c), 6(f), 6(i) and 6(l), the third column, depicts the projected 2-D segmentation overlays from reconstructed surfaces in accordance with an embodiment.
Figure 6D:
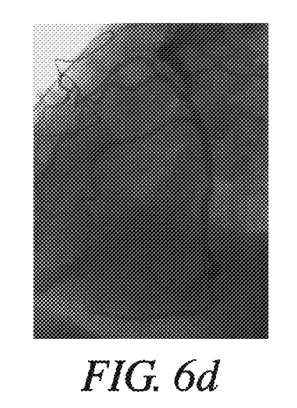
Figure 6E:
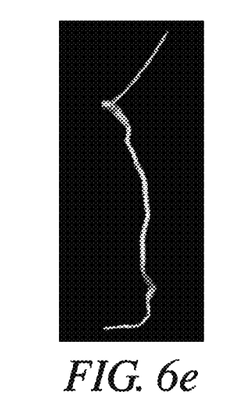
Figure 6F:
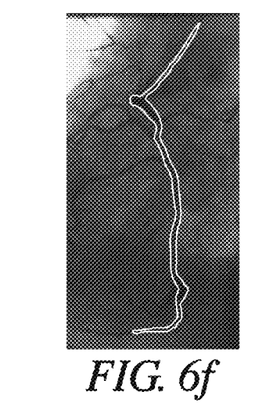
Figure 6G:
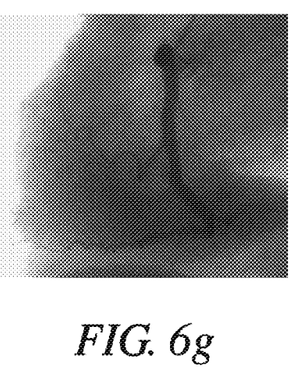
Figure 6H:
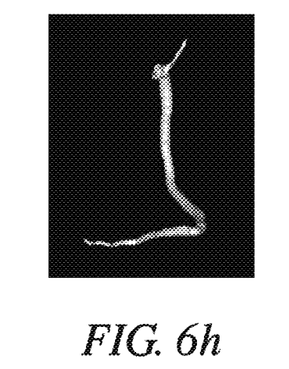
Figure 6I:
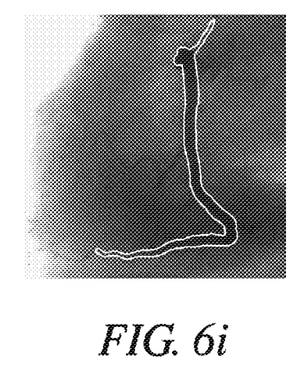
Figure 6J:
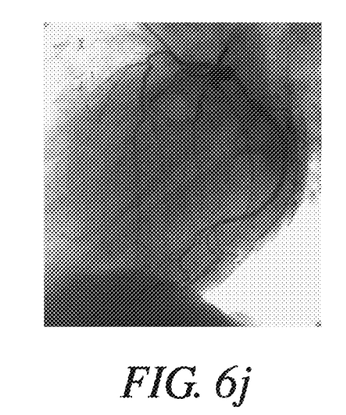
Figure 6K:
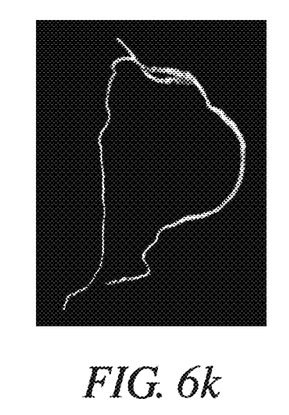
Figure 6L:
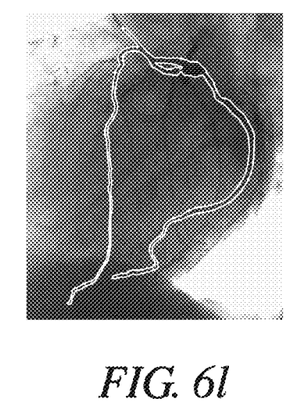

An optimal solution to the surface optimization formulation as defined in Equa. 6 can be transformed into a minimum-cost path formulation within a node-weighted graph, which was first solved in work by Wu, X., Chen, D. Z.: Optimal Net Surface Problems With Applications (see Proc. 29th Int'l Colloquium Automata, Languages, and Programming (ICALP). p. 10291042 (2002)) (hereinafter referred to as Wu). In Wu, the minimum-cost path is sought by finding the most upper graph nodes of a minimum closed set. The Wu method is then utilized in solving a segmentation problem. In an embodiment disclosed herein, a similar graph representation as proposed in Wu is utilized. FIG. 5(d) depicts such a graph representation as employed in an embodiment herein. Each column of the graph of FIG. 5(d) represents a vertex (V1, V2, etc.) of the mesh 504 and corresponds to a searching profile. Graph nodes (N1, N2, etc.) represent sampling points. Cost $w(v_i, S(v_i))$ is assigned to each node. Via iteration of the method disclosed herein, the minimum closed set problem and its dual, the maximum flow problem, is solved by a polynomial-time implementation (algorithm), utilizing such methods as disclosed in Boykov, Y., Kolmogorov, V.: An Experimental Comparison Of Min-Cut/Max-Flow Algorithms For Energy Minimization In Vision (IEEE Trans Pattern Anal Mach Intell 26 (9), 1124-1137 (2004)).

With reference briefly back to FIGS. 5(a)-5(d), which provide an overview of graph structure reconstruction: FIG. 5(a) depicts a synthetic mesh surface (e.g. tubular shape) 502; FIG. 5(b) depicts a mesh zoom-in 504; FIG. 5(c) depicts vessel point sampling in 3-D space 506 as performed along a searching profile (e.g. vertex normal direction) for a vertex $V_i$; and, FIG. 5 (d) depicts a graph structure 508 constructed based on sampling nodes. Graph nodes "N" of the same vertex "V" are intraconnected from top to bottom. The smoothness is enforced by inter-connecting nodes from neighboring columns under a distance $\Delta$.

In the definition of Eq. 6, $w(v_i, S(v_i))$ is a cost function and describes the unlikeliness that a node is on the vessel surface. To resolve this cost function, we employ vessel boundary unlikeliness based cost $w_e(v_i, S(v_i))$ and vessel lumen (region) unlikeliness based cost $w_r(v_i, S(v_i))$. The combination of these two costs is formulated as follows:

$$w(v_i, S(v_i)) = (\alpha)(w_e(v_i, S(v_i))) + (1-\alpha)(w_r(v_i, S(v_i))), \quad \text{Equa. 7}$$

where $\alpha \in [0, 1]$ is a weighting (balance) parameter between boundary-based cost and region-based cost. The boundary-based cost is defined as follows:

$$w_e(v_i, S(v_i)) = (1 - p_e(v_i, S(v_i))), \quad \text{Equa. 8}$$

where $p_e \in [0, 1]$ is the probability that a node belongs to a vessel boundary. The probability $p_e$ can be any normalized value depicting the likeliness of the vessel boundary. The region-based cost is defined as follows:

$$w_r(v_i, S(v_i)) = \sum_{S(v_i)' \leq S(v_i)} (1 - p_v(v_i, S(v_i)')) + \sum_{S(v_i)' > S(v_i)} (1 - p_{nv}(v_i, S(v_i)')), \quad \text{Equa. 9}$$

where $p_v \in [0, 1]$ is the probability that a node belongs to a vessel, and $p_{nv} \in [0, 1]$ is the probability that a node does not belong to a vessel. The probability $p_v$ can be any normalized value depicting the likeliness of the vessel, and the probability $p_{nv}$ can be any normalized value depicting the likeliness of the none vessel region.

In an embodiment, the probability $p_e$ can be defined by the following equation:

$$p_e = \sum_{j=1}^{m} u^{S(vi),j} p_e^j(Q(a_j, S(v_i))), \quad \text{Equa. 10}$$

where $a_j$ is computed based on Eq. 5, $u^{S(vi),j}$ denotes the visibility of 3-D surface point $S(vi)$ on image $j$, and $p_e^i$ denotes a vessel boundary probability map of view $j$. In an embodiment, $u^{S(vi),j}$ is a binary value of 1 or 0, where a value of 1 means the point $u^{S(vi),j}$ is visible on the vessel boundary in image $j$, and a value of 0 means otherwise. In an embodiment, a soft visibility value is utilized as follows:

$$u^{S(vi),j} = \exp((\angle(n_{S(vi)}, v_j) - \pi/2)/\sigma_u), \quad \text{Equa. 11}$$

where $\angle(n_{S(vi)}, v_j)$ is the angle between the normal direction $n_{S(vi)}$ at a predicted surface point $S(v_i)$ and view direction $v_j$ of camera $j$, and $\sigma_u$ is a standard deviation. In an embodiment, $p_e^j$ can be a probability map generated using a machine learning based vessel boundary detector. In an embodiment, $p^j_e$ is a normalized gradient map, and in another embodiment, both gradient magnitude and direction are considered as follows:

$$p^j_e(Q(a_j, S(v_i))) = \{0, \text{ if } [n_{Q(aj,S(vi))} \cdot g^j_{dir}(Q(a_j, S(v_i)))] < 0, \quad g^j_{mag}(Q(a_j, S(v_i))); \text{ if otherwise}\}, \quad \text{Equa. 12}$$

where $n_{Q(aj, S0(vi))}$ is defined in Eq. 13 below, $g^j_{dir}(Q(a_j, S(v_i)))$ and $g^j_{mag}(Q(a_j, S(v_i)))$ are the gradient direction and gradient magnitude at 2-D location $Q(a_j, S(v_i))$ in image j, respectively, and the symbol "·" represents a dot product of the two associated vectors.

$$n_{Q(aj,S0(vi))} = \overrightarrow{<Q(a_j, S_1(v_i)), Q(a_j, S(v_i))>}, \quad \text{Equa. 13}$$

where operator $\overrightarrow{<,>}$ in Equa. 13 represents a vector from the first associated parameter of Q( ) to the second associated parameter of Q( ) and $S_1(v_i)$ is any point on searching profile of vertex $v_i$ below $S(v_i)$ (see FIGS. 5(a)-5(d) for example), where the noted term "below" herein means near to the vessel centerline.

In an embodiment, $p_v$ is defined as follows:

$$p_v = \sum_{j=1}^{m} w^j p^j_v(Q(a_j, S(v_i))), \quad \text{Equa. 14}$$

where $p^j_v$ denotes a vessel region probability map of view j, and $w^j$ defines the weight of an individual projected response ($p^j_v$) in the vessel region confidence $p_v$.

In an embodiment, $p_{nv}$ is defined as follows:

$$p_{nv} = \sum_{j=1}^{m} w^j p^j_{nv}(Q(a_j, S(v_i))), \quad \text{Equa. 15}$$

where $p^j_{nv}$ denotes a known vessel region probability map of view j, defines the weight of an individual projected response ($p^j_{nv}$) in the known vessel region confidence $p_{nv}$.

In an embodiment, $p_{nv} = (1-p_v)$, thereby avoiding computation of Eq. 15. In an embodiment, $p^j_v$ is a probability map generated using a machine learning based vessel detector. In an embodiment, $p^j_v$ can be a normalized vesselness response map based on a method proposed in the work of Frangi, A. F., Niessen, W. J., Vincken, K. L., Viergever, M. A.: Multiscale Vessel Enhancement Filtering, in: MICCAI 1998, pp. 130-137 (1998).

Experimental results of an embodiment of the method disclosed herein are depicted herein with reference to FIGS. 6(a)-6(l), which show examples of coronary vessel surface reconstruction from a limited number of 2-D rotational X-ray angiography images. For example, the first column, FIGS. 6(a), 6(d), 6(g) and 6(j), shows original images from four different patients. The second column, FIGS. 6(b), 6(e), 6(h) and 6(k), shows reconstructed vessel surfaces from the same view as acquired original images via an embodiment of the method disclosed herein. And, the third column, FIGS. 6(c), 6(f), 6(i) and 6(l), shows the projected 2-D segmentation overlays from reconstructed surfaces. As can be seen, the 3-D coronary artery tree surface reconstruction method disclosed herein using a limited number of 2-D rotational X-ray angiography images produces resulting images that correlate well with actual patient associated anatomies, as depicted by the third column of overlays in FIGS. 6(c), 6(f), 6(i) and 6(j).

With respect to the foregoing, it will be appreciated that a method to reconstruct a vessel surface from a limited number of rotational X-Ray angiography images is disclosed. The method disclosed compensates rigid and non-rigid transformations due to breathing and cardiac motion across different 2-D projection views. The method assumes that most of non-rigid vessel deformation is compensated for by ECG gating, that most of the rigid transformations are compensated for in a bundle adjustment based method, and that the remaining transformation differences are compensated for by an optimal graph search based optimization framework. An embodiment determines an optimal surface reconstruction in 3-D space, which avoids having to perform 2-D vessel segmentation and having to find 2-D vessel boundary correspondence.

Figure 7:
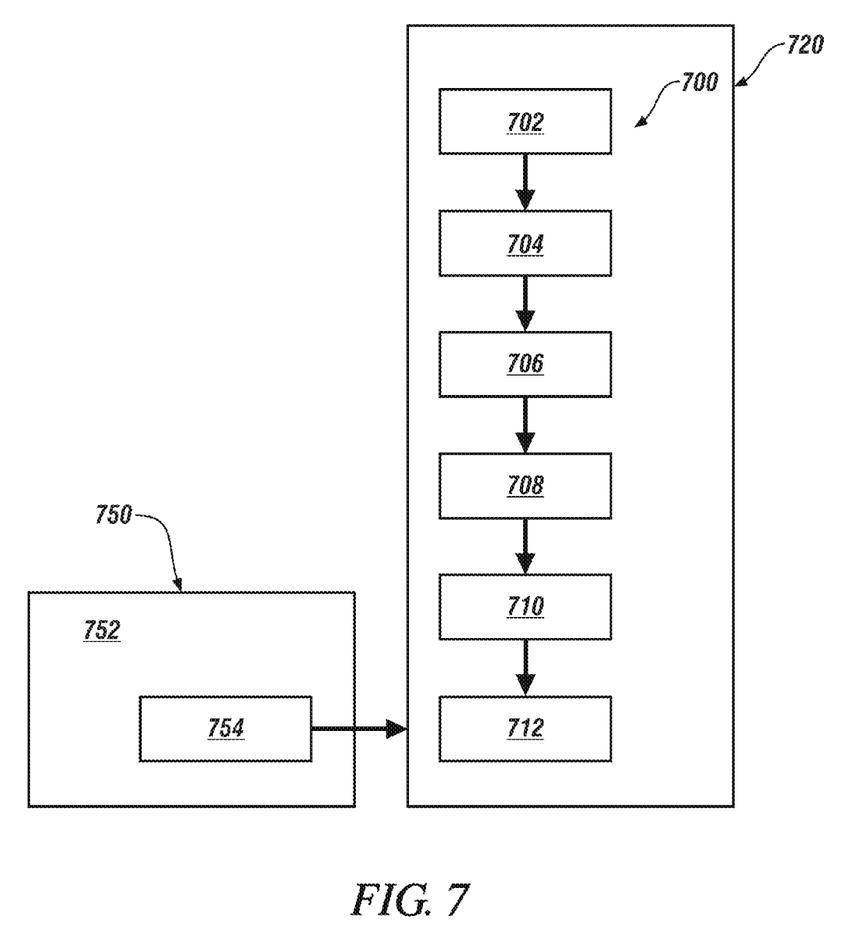
FIG. 7 depicts a method and system in accordance with an embodiment.

In view of the foregoing, and with reference to FIG. 7, it will be appreciated that an embodiment of the invention includes the following.

An embodiment includes a method 700 for reconstructing 3-D vessel geometry of a vessel, comprising: receiving 702 a plurality of 2-D rotational X-ray images of the vessel; extracting 704 vessel centerline points for normal cross sections of each of the plurality of 2-D images; establishing 706 a correspondence of the centerline points; constructing 708 a 3-D centerline vessel tree skeleton of the vessel; constructing 710 an initial 3-D vessel surface having a uniform radius normal to the 3-D centerline vessel tree skeleton; and constructing 712 a target 3-D vessel surface by deforming the initial vessel surface to provide a reconstructed 3-D vessel geometry of the vessel.

An embodiment includes a computer program storage medium 720 comprising a non-transitory computer readable medium having program code executable by a processing circuit for implementing the method 700.

An embodiment includes an apparatus 750 for reconstructing 3-D vessel geometry of a vessel, comprising: a computer controlled machine 752 comprising a processing circuit 754; computer readable executable instructions 720, which upon loading into the processing circuit causes the machine to be responsive to the executable instructions to facilitate implementation of the method 700.

In an embodiment, the method 700 is facilitated by the processing circuit 754 that is responsive to machine readable executable instructions 720 which when executed by the processing circuit 754 facilitates at least the steps 702, 704, 706, 708, 710, 712 of the method 700 to reconstruct 3-D vessel geometry of the vessel 106.

Figure 8A:
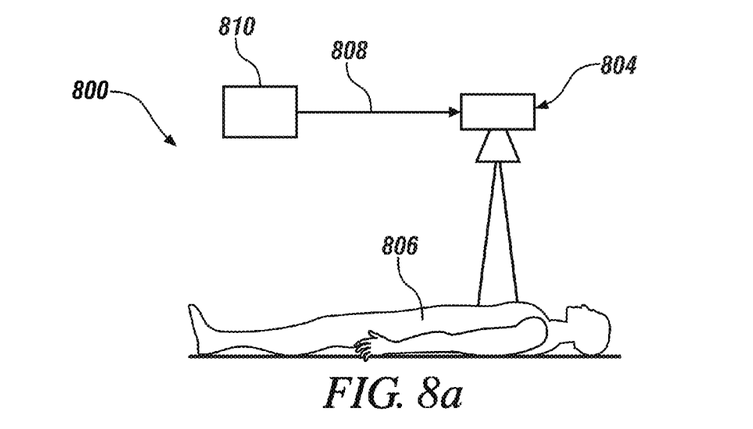
FIGS. 8(a), 8(b) and 8(c), depict an apparatus for capturing 2-D rotational X-ray angiography images in accordance with an embodiment.
Figure 8B:
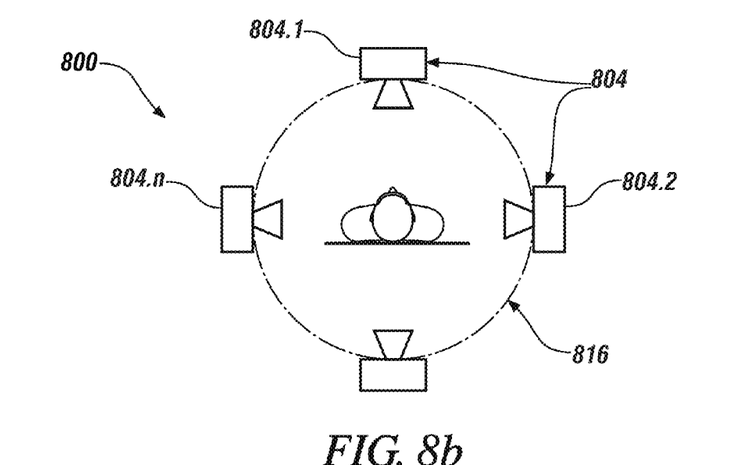
Figure 8C:
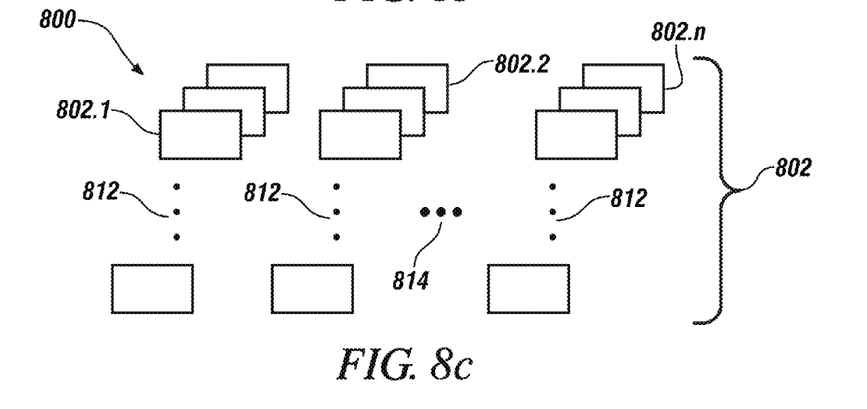

In view of the foregoing, and with reference to FIGS. 8(a), 8(b) and 8(c), it will be appreciated that an apparatus 800 is used to capture 2-D rotational X-ray angiography images 802 of a patient 806 in accordance with an embodiment using a 2-D rotational X-ray machine (also herein referred to as a camera) 804, where the 2-D rotational X-ray machine 804 is controlled using ECG signals or ECG gated acquisition signals 808 from ECG machine 810. FIG. 8(a) depicts a side view the patient 806 and camera 804, FIG. 8(b) depicts an end view of the same patient 806 and camera 804 shown in four positions, and FIG. 8(c) depicts images 802 produced by the camera 804. A first set of images 802.1 are received from a first camera position 804.1, a second set of images 802.2 are received from a second camera position 804.2, and an nth set of images 802.n are received from an nth camera position 804.n. Ellipses 812 represent a plurality of respective sets of images 802 from a given camera 804 position, and ellipses 814 represent a plurality of respective sets of images 802 from a plurality of positions of a given camera 804 as it rotates 816 about the patient 806.

In view of the foregoing, it will be appreciated that an embodiment may be embodied in the form of computer-implemented processes and apparatuses for practicing those processes. An embodiment may also be embodied in the form of a computer program product having computer program code containing instructions embodied in tangible media, such as floppy diskettes, CD-ROMs, hard drives, USB (universal serial bus) drives, or any other computer readable storage medium, such as random access memory (RAM), read only memory (ROM), erasable programmable read only memory (EPROM), electrically erasable programmable read only memory (EEPROM), or flash memory, for example, wherein, when the computer program code is loaded into and executed by a computer, the computer becomes an apparatus for practicing the invention. An embodiment may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing the invention. When implemented on a general-purpose microprocessor, the computer program code segments configure the microprocessor to create specific logic circuits. A technical effect of the executable instructions is to reconstruct a 3-D coronary artery tree surface from a limited number of 2-D rotational X-ray angiography images.

While the invention has been described with reference to exemplary embodiments, it will be understood by those skilled in the art that various changes may be made and equivalents may be substituted for elements thereof without departing from the scope of the claims. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed example embodiments and, although specific terms may have been employed, they are unless otherwise stated used in a generic and descriptive sense only and not for purposes of limitation, the scope of the claims therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item. Additionally, the term "comprising" as used herein does not exclude the possible inclusion of one or more additional features.

What is claimed is:

1. A method for reconstructing 3-D vessel geometry of a vessel, comprising:
   receiving a plurality of 2-D rotational X-ray images of the vessel;
   extracting vessel centerline points for normal cross sections of each of the plurality of 2-D images;
   establishing a correspondence of the centerline points;
   constructing a 3-D centerline vessel tree skeleton of the vessel;
   constructing an initial 3-D vessel surface having a uniform radius normal to the 3-D centerline vessel tree skeleton; and
   constructing a target 3-D vessel surface by deforming the initial vessel surface to provide a reconstructed 3-D vessel geometry of the vessel,
   wherein the extracting vessel centerlines is accomplished in a form of ordered point sets, $S_i$, from angiographic images, where i is the $i^{th}$ image, and each point set $S_i$ is a projection of a transformed 3-D centerline model M according to the following:

$$S_i = P_i T(M, \theta_i),$$

wherein $P_i$ is a camera projection operator corresponding to image i, and $T(M, \theta_i)$ is a defined transformation model;
   wherein given M and $S_i$, Gaussian mixture models (GMM) are employed to find transformations $T(M, \theta_i)$ that minimize the following cost function:

$$J(S_i, M, \theta_i) = \int (GMM(S_i) - GMM(P_i T(M, \theta_i))^p dx,$$

wherein $J(Si, M, \theta_i)$ is an energy function that measures a distance of two Gaussian mixture models (GMM) where $p \in [0, 2]$.

2. The method of claim 1, wherein:
   the vessel is a coronary artery.

3. The method of claim 1, wherein:
   the 2-D images have a same cardiac phase.

4. The method of claim 1, wherein:
   the 2-D images are received using ECG signals or ECG gated acquisition signals.

5. The method of claim 1, wherein:
   the 2-D images are angiography images.

6. The method of claim 1, wherein:
   the extracting vessel centerlines is accomplished using a technique of model-guided extraction.

7. The method of claim 1, wherein:
   the establishing the correspondence of centerline points is accomplished using a bipartite graph that corresponds to a linear assignment process that finds a matching vessel point for every projected model point in each image, wherein the bipartite graph represents a first set of vertices (i) that represent transformed, projected model points of the vessel centerline points, and a second set of vertices (j) that represent associated segment points of a prior 3-D vessel shape of the vessel segmented from a DynaCT volume and DynaCT reconstruction, wherein weights at edges, cij, of paired vertices of the first and second sets of vertices are computed using a distance of spatial locations of the respective vertices $d_{ij}$ according to the following:

$$c_{i,j} = \{d_{i,j} \text{ if } d_{i,j} < dth; \infty \text{ if } d_{i,j}\_d_{th}\},$$

wherein $d_{th}$ is a defined distance threshold.

8. The method of claim 7, wherein:
   the constructing the 3-D centerline vessel tree skeleton is accomplished according to the following:

$$\min_{a_j, b_i} \sum_{i=1}^{n} \sum_{j=1}^{m} k^{i,j} d(Q(a_j, b_i), x^{i,j}),$$

wherein: n is a number of 3-D points that are seen in m views; camera (j) is parameterized by a vector $a_j$; $b_i$ is the $i^{th}$ centerline point; $Q(a_j, b_i)$ is the projection of 3-D point $b_i$ on image (j); $x^{i,j}$ is the $i^{th}$ 2-D centerline point measurement on image (j); d( , ) is a Euclidean distance between the associated points $Q(a_j, b_i)$ and $x^{i,j}$; and, $k^{i,j} \in [0, 1]$ is a confidence measurement of $x^{i,j}$.

9. The method of claim 8, wherein:
the constructing the initial 3-D vessel surface is accomplished by generating a point cloud of circles around and perpendicular to a tangential direction of the associated centerline, each one of the point cloud of circles having a defined radius r, and computing an initial surface mesh via a Poisson surface reconstruction method using the point cloud of circles.

10. The method of claim 9, wherein:
the constructing the target 3-D vessel surface is accomplished using 2-D information through 3-D to 2-D projection to deform the initial 3-D vessel surface according to the following:

$$T=\{S(v_i) | i=1 \ldots L\},$$

wherein T represents the initial 3-D vessel surface having radius r, where L is the number of vertices ($v_i$), i is an iterative parameter, and $S(v_i)$ is a sampling point along a searching profile for ($v_i$), wherein a minimum-surface cost function $w(v_i, S(v_i))$, subject to smoothness constraints $|S(v_i)-S(v_j)| \leq \Delta$, is solved via the following:

$$T^* = \mathrm{argmin} \Sigma w(v_i, S(v_i))$$
$$T\, i = 1 \ldots L$$
$$\text{subject to } |S(v_i) - S(v_j)| \leq \Delta,$$

wherein T* represents the target 3-D vessel surface, and $\Delta$ is a smoothness constraint that requires that the surface's position between neighboring vertices ($v_i$) and ($v_j$) does not change more than a constant distance $\Delta$.

11. The method of claim 10, wherein the cost function $w(v_i, S(v_i))$ describes the unlikeliness that a node is on the target vessel surface and is resolved according to the following:

$$w(v_i, S(v_i)) = (\alpha)(w_e(v_i, S(v_i))) + (1-\alpha)(w_r(v_i, S(v_i))),$$

wherein $\alpha \in [0, 1]$ is a weighting (balance) parameter between a boundary-based cost $w_e(v_i, S(v_i))$ and region-based cost $w_r(v_i, S(v_i))$, the boundary-based cost being defined as follows:

$$w_e(v_i, S(v_i)) = (1 - p_e(v_i, S(v_i))),$$

wherein $p_e \in [0, 1]$ is the probability that a node belongs to a vessel boundary, wherein the probability $p_e$ is a normalized value depicting the likeliness of the vessel boundary, wherein the region-based cost is defined as follows:

$$w_r(v_i, S(v_i)) = \sum_{S(v_i)' \leq S(v_i)} (1 - p_v(v_i, S(v_i)')) + \sum_{S(v_i)' > S(v_i)} (1 - p_{nv}(v_i, S(v_i)')),$$

wherein $p_v \in [0, 1]$ is the probability that a node belongs to a vessel, and $p_{nv} \in [0, 1]$ is the probability that a node does not belong to a vessel.

12. The method of claim 11, wherein:
probability $p_e$ is defined by the following:

$$p_e = \sum_{j=1}^{m} u^{S(vi),j} p_e^j(Q(a_j, S(v_i))),$$

wherein $u^{S(vi),j}$ denotes a visibility of a 3-D surface point S(vi) on image j, and $p^j_e$ denotes a vessel boundary probability map of view j, wherein $u^{S(vi),j}$ is a binary value of 1 or 0, where a value of 1 means the point $u^{S(vi),j}$ is visible on the vessel boundary in image j, and a value of 0 means otherwise;
wherein a soft visibility value is utilized as follows:
$$u^{S(vi),j} = \exp((\angle(n_{S(vi)}, v_j) - \pi/2)/\sigma_u),$$

wherein $\angle(n_{S(vi)}, v_j)$ is an angle between a normal direction $n_{S(vi)}$ at a predicted surface point $S(v_i)$ and view direction $v_j$ of camera j, and $\sigma_u$ is a standard deviation;
wherein $p^j_e$ is either: a probability map generated using a machine learning based vessel boundary detector; a normalized gradient map; or, both gradient magnitude and direction are considered as follows:
$$p^j_e(Q(a_j, S(v_i))) = \{0, \text{ if } [n_{Q(aj, S(vi))} \cdot g^j_{dir}(Q(a_j, S(v_i)))] < 0,$$
$$g^j_{mag}(Q(a_j, S(v_i))); \text{ if otherwise}\},$$

wherein $g^j_{dir}(Q(a_j, S(v_i)))$ and $g^j_{mag}(Q(a_j, S(v_i)))$ are a gradient direction and gradient magnitude at 2-D location $Q(a_j, S(v_i))$ in image j, respectively, wherein $n_{Q(aj, S0(vi))}$ is defined as follows:
$$n_{Q(aj, S0(vi))} = \overrightarrow{<Q(a_j, S_1(v_i)), Q(a_j, S(v_i))>},$$
wherein $S_1(v_i)$ is any point on searching profile of vertex $v_i$ below $S(v_i)$.

13. The method of claim 1, wherein:
the establishing the correspondence of centerline points is accomplished using a prior 3-D vessel shape segmented from a DynaCT volume and DynaCT reconstruction.

14. The method of claim 1, wherein:
the establishing the correspondence of centerline points is accomplished using vessel centerline tangents and normals.

15. The method of claim 1, wherein:
the constructing the 3-D centerline vessel tree skeleton is accomplished using 2-D points of the extracted vessel centerlines using a bundle adjustment based approach.

16. The method of claim 1, wherein:
the constructing the target 3-D vessel surface is accomplished using a polynomial-time implementation.

17. A computer program storage medium comprising a non-transitory computer readable medium having program code executable by a processing circuit for implementing the method according to claim 11.

18. An apparatus for reconstructing 3-D vessel geometry of a vessel, comprising:
a computer controlled machine comprising a processing circuit;
computer readable executable instructions, which upon loading into the processing circuit causes the machine to be responsive to the executable instructions to facilitate implementation of the method according to claim 11.

* * * * *